United States Patent [19]

Michalevicz

[11] Patent Number: 5,104,653
[45] Date of Patent: Apr. 14, 1992

[54] USE OF HUMAN INTERFERON-BETA FOR STIMULATION OF ERYTHROPOIESIS

[75] Inventor: Rita Michalevicz, Petach Tikvah, Israel

[73] Assignees: Interpharm Laboratories Ltd., Ness-Ziona; Ramot, University Authority for Applied Research and Industrial Development Ltd., Tel-Aviv, both of Israel

[21] Appl. No.: 495,027

[22] Filed: Mar. 16, 1990

[30] Foreign Application Priority Data

Mar. 19, 1989 [IL] Israel ..................................... 89662

[51] Int. Cl.$^5$ ...................... C07K 13/00; A61K 37/66
[52] U.S. Cl. ..................................... 424/85.6; 530/351
[58] Field of Search .......................... 530/351; 424/85.6

[56] References Cited

PUBLICATIONS

Ortega et al. *Exp. Hemat.* 7(3) pp. 145–150 (1979).
Lutton et al. *J. Lab Clin Med* 96(2) pp. 328–333 (1980).
Klimpel et al. The IFN System: A Current Review, Baron, ed., Univ. of Texas Press (1987) pp. 261–267.
Broxmeyer, H. E. et al., "Comparative Analysis of the Influences of Human Gamma, Alpha and Beta Inteferons On Human Multipotential (CFU-GEMM), Eruthroid (BFU-E) and Granulocyte-Macrophage (CFU-GM) Progenitor Cells", The Journal of Immunology, vol. 131, No. 3, pp. 1300–1305, 1983.
Neumann, H. A. et al., "Effect of Interferon on Pluripotent Hemopoietic Progenitors (CFU-GEMM) Derived from Human Bone Marrow", *Exp. Hematol.*, vol. 10, No. 7, 587–590, 1982.
Gidali, J. et al., "Proliferation Inhibition of Murine Pluripotent Haemopoietic Stem Cells By Interferon Or Poly I:C", *Cell Tissue Kinet.*, 14, 1–7, 1981.
van t'Hull, E. et al., "Influence of Interferon Preparations on the Proliferative Capacitiy of Human and Mouse Bone Marrow Cells in Vitro", *Cancer Research*, 911–914, Apr. 1978.
Gallien-Lartigue, O. et al., "Strain Dependence of the Antiproliferative Action of Interferon on Murine Erythroid Precursors", *Science*, vol. 292–293, 1980.
McNeill, T. A. et al., "The Relationship Between Serum Interferon and an Inhibitor of Mouse Haemopoietic Colines in vitro", *Immunology*, vol. 21, 761–766, 1971.
Fleming, W. A. et al., "The Effects of an Inhibiting Factor (Interferon) on the in vitro Growth of Granulocyte-Macrophage Colonies", *Immunology*, vol. 23, 429–437, 1972.
Greenberg, P. L. et al., "Cytotoxic Effects of Interferon in Vitro on Granulocytic Progenitor Cells", *Cancer Research*, 37, 1794–1799, 1977.
Michalevisz, R. et al., "Interferons regulate the in vitro differentiation of multilineage lympho-myeloid stem cells in hairy cell leukemia", *Proc. Natl. Acad. Sci, USA*, vol. 84, 2307–2311, 1987.
Frisch, B. et al., "Bone marrow histology in myelodysplatic syndromes", *Scand J Haematol*, 36, Suppl 45:21–37, 1986.
Michalevicz, R. et al., "Cell Differentiation and Therapeutic Effect of Low Doses of Cytosine Arabinoside in Human Myeloid Leukemia", *Leukemia Research*, vol. 8, No. 5, 783–790, 1984.
Wisch, J. S., et al, "Response of Preleukemic Syndromes to Continuous Infusion of Low-Dose Cytarabine", The New England Journal of Medicine, vol. 309, No. 26, 1599–1602, 1983.
Mehta, A. B. et al., "Treatment of Advanced Myelodysplastic Syndrome with Alfacalcidol", p. 761, Sep. 29, 1984.
Vadhan-Raj, S., et al., "Effects of Recombinant Human Granulocyte-Macrophage Colony-Stimulating Factor in Patients with Myelodysplastic Syndromes", The New England Journal of Medicine, 317, 25, 1545–1552, 1987.
Vellenga, E., et al., "The Effects of GM-CSF and G-CSF in Promoting Growth of Clonogenic Cells in Acute Myeloblastic Leukemia, *Blood*, vol. 69, No. 6, 1771–177"6, 1987.
Carlo-Stella, et al., "Effects of Recombinant α and Interferons on the In Vitro Growth of Circulating Hematopoietic Progenitor Cells (CFU-GEMM, CFU-Mk, BFU-E, and CFU-GM) From Patients With Myelofibrosis With Myeloid Metaplasia", *Blood*, vol. 70, No. 4, 1014–1019, 1987.
Wickramasinghe, S. N., et al, "Alpha-Interferon in Primary Idiopathic Myelofibrosis", *The Lancet*, 1524–1525, Dec. 26, 1987.
Gastl, G., et al, "Interferon-Alpha for Idiopathic Myelofibrosis", *The Lancet*, 765–766, Apr. 2, 1988.

*Primary Examiner*—David L. Lacey
*Assistant Examiner*—Shelly J. Guest
*Attorney, Agent, or Firm*—Browdy and Neimark

[57] ABSTRACT

Interferon-beta, preferably in low doses, is used for stimulation of erythropoiesis in disorders characterized by lack of maturation of progenitor blood cells to red cells.

18 Claims, No Drawings

USE OF HUMAN INTERFERON-BETA FOR STIMULATION OF ERYTHROPOIESIS

The present invention relates to a method for the stimulation of erythropoiesis in patients suffering from disorders characterized by lack of maturation of progenitor blood cells to red cells comprising the administration of human Interferon-beta (IFN-$\beta$) in effective amounts.

All peripheral blood cells arise from a common progenitor cell known as the pluripotent hemopoietic stem cell. An important property of stem cells is self-renewal, which ensures a continuous supply throughout the lifetime of the individual. When required, a pluripotent cell can begin to differentiate, and with successive divisions it loses the capacity for self-renewal, and its progeny becomes committed to a particular line of development. These progenitors will then give rise to all the blood cells capable of functional purposes.

The formation of mature blood cells comes at the end of a process which comprises the proliferation and maturation of specifically commited progenitor cells from each lineage. Pluripotent cells are thus capable of producing a clone consisting of a number of red cells, granulocytes, platelets and lymphocytes, together with their intermediate progenitor cells.

Under normal circumstances, the marrow is able to respond quickly to an increased demand for a particular type of cell. How it does so is the subject of much current research. It is known that the process of proliferation and differentiation of progenitor cells is under the control of several growth stimulants known as hematopoietic hormones, e.g. erythropoietin and several colony-stimulating factors.

Erythropoiesis consists of a process that begins at the stage of early BFU-E (burst-forming unit - erythroid, the earliest red cell precursor) formation, mainly governed by interleukin-3 (IL-3) and subsequently further maturation to CFU-E (colony-forming unit - erythroid) and normoblasts by erythropoietin. Normoblasts mature to reticulocytes and then to erythrocytes, the mature blood cells.

It is known that there may be differences in the age of circulating and bone marrow progenitor cells. The effects of all three types of interferons - alpha, beta and gamma, have been studied by several groups on normal bone marrow progenitor cells. It was found that all three interferons exert a suppressive effect on growth of colony-forming cells from normal bone marrow (Broxmeyer, Hal E. et al. (1983) Comparative analysis of the influences of human gamma, alpha and beta interferons on human multipotential (CFU-GEMM), erythroid (BFU-E) and granulocyte-macrophage (CFU-GM) progenitor cells, J. Immunol. 131:1300–1305). Thus, they have been implicated in the suppression of in vitro colony formation by human and mouse multipotential (CFU-GEMM=colony-forming unit - granulocyte, erythroid, macrophage, megakaryocyte), erythroid (CFU-E) and granulocyte-macrophage (CFU-GM) progenitor cells. (References: Neumann, H. A. and A. A. Fauser (1982) Effect of interferon on pluripotential hemopoietic progenitors (CFU-GEMM) derived from human bone marrow, Exp.Hematol. 10:587: Gidali, J. et al. (1981) Proliferation inhibition of murine pluripotent haemopoietic stem cell by interferon on poly I:C, Cell Tissue Kinet. 14:1; Van't Hull, E. et al. (1978) Influence of interferon preparations on the proliferative capacity of human and mouse bone marrow cells in vitro, Cancer Res. 38:911; Gallien-Lartigue, O. et al. (1980) Strain dependence of the antiproliferative action of interferon on murine erythroid precursors, Science 209:292) McNeill, T. A. and W. A. Fleming, (1971) The relationship between serum interferon and an inhibitor of mouse haemopoietic colonies in vitro, Immunology 21:761; Fleming, W. A. et al. (1972) The effect of an inhibiting factor (interferon) on the in vitro growth of granulocyte-macrophage colonies, Immunology 23:429; Greenberg, P. L. and S. A. Mosny (1977) Cytotoxic effects of Interferon in vitro on granulocytic progenitor cells, Cancer Res. 37:1794).

Interferons were shown to regulate the in vitro differentiation of multilineage lympho-myeloid stem cells circulating in hairy cell leukemia (HCL) (Michalevicz, R. and M. Revel (1987) Interferons regulate the in vitro differentiation of multilineage lympho-myeloid stem cells in hairy cell leukemia, Proc. Natl. Acad. Sci. U.S.A. 84. pp. 2307–2311). Through the modulatory effect of the interferons, stem cells were stimulated to give burst to more progenies, without leading to higher formation of some progeny in particular.

Now, in contrary to earlier findings, it was found that IFN-$\beta$ (also known as IFN-$\beta$1) has an erythropoietic effect on growth of progenitor cells from individuals suffering from several diseases with a very low production of red blood cells. It was also found that IFN-$\beta$ increases burst formation as well as promotes a more rapid maturation toward normoblasts and even late reticulocytes. This could not be inferred from the above study on hairy cell leukemia, which is a malignant transformation of a stem cell leading to lymphopoiesis and reduction of other lineages thus causing pancytopenia and accumulation of hairy cells (preplasmatic cells) in the bone marrow.

Accordingly, the object of the present invention is a method comprising the administration of human IFN-$\beta$ for the stimulation of erythropoiesis in patients suffering from disorders characterized by lack of maturation of progenitor blood cells to red cells.

A further object of the present invention is to provide pharmaceutical compositions comprising IFN-$\beta$ as active ingredient for use in the method of the invention. The compositions comprise IFN-$\beta$ together with a pharmaceutically acceptable carrier, this term including any carrier which does not interfere with the effectiveness of the biological activity of the IFN-$\beta$ and which is not toxic to the host to which it is administered.

The IFN-$\beta$ used according to the invention may be native IFN-$\beta$ produced by induced fibroblast cells or recombinant IFN-$\beta$ (rIFN-$\beta$) produced by genetic engineering techniques. The rIFN-$\beta$ may be produced by prokaryotic, e.g. E. coli cells, or eukaryotic, e.g. chinese hamster ovary (CHO) cells. Preferably, rIFN-$\beta$ produced by CHO cells is used according to the invention.

The compositions comprising IFN-$\beta$ may be administered by parenteral route, such as subcutaneously or preferably intramuscularly. For this purpose, a suitable injectable solution is prepared by any conventional means known in the pharmaceutical arts and being compatible with human interferon administration. For example, an injectable solution may contain sterile isotonic saline, preservatives such as methylparaben or propylparaben, stabilizers such as human serum albumin, pH adjusters, buffers and the like. A wide variety of suitable parenteral vehicles are set forth in the textbook "Remington's Pharmaceutical Sciences" (17 ed., 1985).

As one embodiment of the invention, the compositions are of native IFN-β stabilized with human serum albumin. For this purpose, Frone® (Inter-Lab, Israel and Serono, Italy), a preparation of human IFN-β obtained from superinduced cultures of human diploid foreskin cells, is purified to $10^7$ units per mg protein and then lyophilised with human serum albumin in vials containing $10^6$ IU (1 MU) of IFN-β.

In a preferred embodiment the recombinant IFN-β produced in CHO cells is purified to homogeneity and formulated in injectable forms, together with suitable carriers and stabilizers, such as human serum albumin, mannitol and buffer e.g. acetate buffer.

The compositions to be used in the method of the invention are to be administered preferably in low doses. By "low doses" it is meant to use daily 1 to 3 MU (million units) preferably 2 MU, for patients with about 60 kg bodyweight. For comparison, patients suffering from acute viral diseases are treated daily with 500.000 U of IFN-β or IFN-β per kg of bodyweight (30 MU/60 kg) and from chronic viral diseases with 3-10 MU/60 kg bodyweight. The low dose of 1-2 MU may be used daily for months or, if the patient condition improves after one month, the dose of 1-2 MU may be given twice or thrice weekly for another 3 months or more.

In the method of treatment of the invention, the dose will depend on the severity of the disease and the condition of the patient. The composition may be injected intramuscularly, or subcutaneously.

In another embodiment of the invention, IFN-β is administered with interleukin-3 (IL-3), when the patient is defective in this interleukin. IL-3 may be administered prior to, together with or after the administration of IFN-β. The daily dose of IL-3 will depend on the condition of the patient, e.g. 50 μg per kg of bodyweight. It may be administered by infusion.

The compositions of the invention are for use in disorders where there is a lack of maturation of progenitor blood cells to red cells and the IFN-β thus acts as an adjuvant erythropoietic maturation factor.

Disorders that may respond to treatment with IFN-β include myelodisplastic syndromes, chronic myelomonocytic leukemia (CMML), chronic myeloid leukemia (CML) and all anemias caused by chronic disorders, such as chronic infectious disorders, rheumatoid arthritis, etc.

The compositions of the invention may be used in the treatment of myelodysplastic syndromes. The term comprises a set of diseases which include anemia, macrocytic peripheral red blood cells in general, megaloblastic or diserythropoietic erythropoiesis and/or ringed sideroblasts (sideroblastic anemia), and abnormal megakaryopoiesis and/or disordered granulopoiesis.

The myelodysplastic syndromes may be subclassified into 5 types: refractory anemia (RA), refractory anemia with ringed sideroblasts (RARS), chronic myelomonocytic leukemia (CMML), refractory anemia with excess blasts (RAEB) and RAEB in transformation.

In some of these syndromes patients may be asymptomatic and only slight macrocytic anemia leads to a correct diagnosis. In others, pancytopenias and need for blood transfusion may constitute a major medical problem or severe pancytopenia may evolve to leukemia. In many cases, patients with myelodysplastic syndromes will never develop acute leukemia for many years (more than 10) following the diagnosis of inefficient hematopoiesis.

Several studies have demonstrated that this group of hematologic anomalies represents a disorder affecting the stem cells. In general, poor culture growth of progenitor cells characterizes the patients. Contradictory reports do exist, but can probably stem from lack of homogeneity in culture techniques. It has also been suggested that colony-forming cells (progenitor cels) from these patients are sensitive to colony-stimulating factors (CSFs).

Since there is no specific effective therapy for the syndromes described, supportive therapy constitutes the major task of the hematologist. Blood transfusions help relieve symptomatology due to severe anemia, but carries risk for iron overload and hemochromatosis, besides other complications such as viral infections and adverse reactions due to blood transfusions. Platelets and granulocytes transfusions are rarely effective and prophylactic therapy has no role. Rare responses to corticosteroids and rarer responses to androgens have been described. Cytotoxic chemotherapy is not indicated during the benign phases and its role is not certain when leukemia develops. The relatively high age group together with expected side effects from chemotherapy make this approach not attractive. Alternatively low doses of cytosine arabinoside have recently been used and in some studies some responses were obtained, (Frisch, B. and B. Bartl (1986) Bone marrow histology in myelodysplastic syndromes, Scan. J. Hematol. 36. Supp. 45:21–37; Michalevicz, R. et al. (1984) Cell differentiation and therapeutic effect of low doses of cytosine arabinoside in human myeloid leukaemia, Leuk.Res. 8:783-790), but with severe pancytopenia occurring in some cases (Wisch. J. S. et al. (1983) Response of preleukaemic syndrome to continuous infusion of low dose cytosine arabinoside, N.Eng.J.Med. 309:1599–1602).

Other investigational approaches have been tried in the past and included open trials with Vit D3 (1,25-dihydroxy Vit Ds) and retinoic acid (13-cis) with no beneficial effects (Mehta, A. B. et al. (1984) Treatment of advanced myelodysplastic syndrome with alfacalidol, Lancet 2:761). Recent studies focusing on myelodysplastic syndromes have shown that recombinant human granulocyte-macrophage colony-stimulating factor can promote hematologic improvement in short term observation (Vadhan Raj S. et al. (1987) Effects of recombinant human granulocyte-macrophage colony stimulating factor in patients with myelodysplastic syndromes, N.Eng.J.Med. 317:1545–1552). However, other groups reported contradictory observations and one should also be cautious when administering GM-CSF in the group of preleukemia patients since leukemic blasts can be stimulated to grow in presence of GM-CSF (Vellenga, E. et al. (1987) The effects of GM-CSF and G-CSF in promoting growth of clonogenic cells in acute myeloblastic leukemia, Blood, 69:1771–1776).

The compositions of the invention may also be used in the treatment of idiopathic myelofibrosis. This disease is a chronic myeloproliferative disorder related to clonal expansion of a pluripotent hematopoietic progenitor cell and associated with secondary marrow fibrosis. No definitive treatment has yet been devised for this condition. There is a marked variability in clinical severity and in survival. Like the myelodysplastic syndromes and like polycythemia vera and chronic myeloid leukemia, myelofibrosis is a disease affecting the multipotent stem cell. This disorder shows besides excessive proliferation of normal stem cells, defects in stem cell maturation. Anemia and large spleen are usually a constant feature of this disease.

The effects of IFN-$\beta$ alone and with IFN-gamma on growth of colony forming cells from patients with myelofibrosis were studied in vitro and it seems that a suppressive effect was obtained (Carlo-Stella, C. E. et al. (1987), Effects of recombinant alpha and gamma interferons on the in vitro growth of circulating hematopoietic progenitor cells (CFU-GEMM, CFU-Mk, BFU-E and CFU-GM) from patients with myelofibrosis with myeloid metaplasia, Blood 70:1014–1019). Since in this group of patients there is an increase in the number of colony-forming cells (CFU-GM, CFU-Mix, BFU-E) it seems that the patient can benefit from reducing the number of progenitor cells. In vivo treatment of either individual cases or small groups with IFN-o has been reported and the results were not very encouraging - either no response or some reduction in spleen size, but myelosuppression was observed (Wickramasinghe, S.N. et al. (1987) Alpha interferon in primary idiopathic myelofibrosis, Lancet p. 1524: Gastl, G. et al. (1988) Interferon-alpha for idiopathic myelofibrosis, Lancet, pp. 765–766).

To better determine whether the hematopoietic effect in general and the erythropoietic one in particular are peculiar to some disease states involving hematopoiesis or whether it represents a universal erythropoietic activity, the effects of IFN-$\beta$ were checked on circulating and bone marrow progenitor cells. Both undepleted and monocyte depleted samples were tested. Attention was given to differences that could possibly occur between circulating versus bone marrow progenitors either in the stem cells themselves or due to different surrounding (homing).

According to the invention, it has been demonstrated that IFN-$\beta$, in particular in low doses, has an erythropoietic effect on growth of progenitor cells obtained from patients with sideroblastic and refractory anemia and in myelofibrosis. This is an unusual observation since, as said before, interferons were shown by several authors to suppress normal hematopoiesis in vitro.

The effects of rIFN-$\beta$ on the growth of erythroid progenitors in vitro was tested using the colony formation assay. The assay consists of growing cells in a semi-solid medium (methylcellulose) for two weeks: In this assay, in order to grow erythroid progenitors, conditioned medium consisting of phytohemagglutinin-treated lymphocytes (PHA-LCM) is used as source for hematopoietic growth factors. One can almost completely replace the effects of PHA-LCM on erythroid growth when using rIL-3. It should be stressed that the hormone erythropoietin is essential for growth of mature red cell progenitors and was therefore used in all the cultures in this study.

The growth of erythroid precursors termed BFU-E (burst forming units erythroid) was monitored by identification and counting of the colonies under the inverted microscope as well as by removal and proper staining of colonies where and when necessary. The number of mixed colonies represents the number of earlier progenitor cells (containing erythroid as well as one or more other lineage cells) and granulocytic/macrophage colonies were also assessed in the cultures.

The invention will now be illustrated by the following examples:

Colony-Forming Cultures for Hematopoietic Progenitors

Cells were cultured essentially by the following procedure: peripheral blood mononuclear cells (PBMC) were separated from heparinized blood by Ficoll-/Hypaque (Pharmacia) centrifugation and washed. Cells that did not adhere to plastic dishes after 2 hrs were plated at $4 \times 10^5$ cells per ml (monocyte depleted) in Iscove's Modified Dulbecco's medium (IMDM Gibco) with 20.Z (vol/vol) fresh human plasma (single donor), 0.9.% methyl cellulose, 20$\mu$M 2-mercaptoethanol, erythropoietin at 0.5U/ml (step III, Connaught Laboratories, Willowdale, ON), and 10.% (vol/vol) fetal calf serum supplemented by 7.5% (vol/vol) phytohemagglutinin-stimulated leukocyte conditioned medium PHA-LCM (supernatant of PBMC from healthy donors after 7 days of culture at $10^6$ cells per ml with 1% phytohemagglutinin in IMDM and 10.% (vol/vol) fetal calf serum) as the source of multicolony-stimulating growth factors. Formation of colonies was followed for 14 days at 37° C. in humidified 5.% COZ/95.% air. Where indicated various IFNs were added at day 0. Recombinant (r)IFN-$\beta$ -c was produced in E. coli and purified to homogeneity (10° international units/mg). rIFN-$\beta$ and rIFN-gamma were both produced in CHO cells and purified to homogeneity. T-cell depletion was performed by using the E rosette technique and Ficoll recentrifugation. The remaining monocyte and/or T depleted cells were checked for homogeneity and more than 95% purity was achieved.

Analysis of colonies

Colonies are classified as CFU-GEMM (colony-forming unit-granulocyte/ erythroid/macrophage/-megakaryocyte) or CFU-Mix, CFU-GM (colony-forming unit-granulocyte/macrophage) and BFU-E (burst-forming unit-erythroid). Mixed colonies may contain one or more lineage and not necessarily all types.

When necessary, multilineage refringent colonies were removed with a fine micropipette for identification, spread on slides and stained appropriately with Wright-Giemsa, cytochemistry or with monoclonal antibodies. Briefly, after fixation with paraformaldehyde, the specific monoclonal antibodies are added for 30 min. and after 3 washes with PBS, the second layer antibody (FITC) added appropriately. Cells are then counted using a Zeiss immunofluorescence microscope. Monoclonal antibodies for glycoprotein IIb/IIIa were used for megakaryocyte identification. Pooled colonies were washed and stained live with the monoclonal antibodies B1 (CD20, Coulter) or fixed and stained with RFB7 monoclonal antibodies (CD20$\mu$) and fluorescein-conjugated goat anti-mouse IgG or IgMFab as described by E. L. Raefsky et al (19S5), J. Immunol. 135:2507–2512. Other antibodies used were RFT-2 (CD7$\tau_2$) antibodies from the Royal Free Hospital and anti-TAC monoclonal antibodies from the National Institute of Health. Staining for tartrate-resistant acid phosphatase was as described by B. Torok-Storb et al. (1987) Blood 69:629–633.

Blood samples and bone marrow aspirates from several patients were analyzed, including from five patients with sideroblastic anemia, five patients with refractory anemia without any evidence for incipient leukemia, eight patients with myelofibrosis, and normal controls (both bone marrow and peripheral blood).

Effect on growth of hematopoietic colonies in various diseases by interferons Peripheral blood mononuclear cells of normal individuals and of patients with lymphoma, chronic myeloid leukemia (CML) and hairy cell leukemia (HCL) were cultured in vitro for 14 days as described above. Interferon was added at day 0 and the doses used in these experiments were 100 U/ml for alpha, beta and gamma IFNs. Some experiments were made also with 500 U/ml interferon. The results are shown in Table I. Even at 100 U/ml IFN-$\beta$ did not suppress hematopoiesis as IFN-$\alpha c$ and on both CML and HCL there was a promoting effect on BFU-E growth (50 and 25 per cent, respectively). Thus IFN-$\beta$ has a lesser suppressive effect on hematopoiesis than IFNs $\alpha$-c and gamma even when used at 100 U/ml.

TABLE I
EFFECT OF IFN ON GROWTH OF HEMATOPOIETIC COLONIES IN VARIOUS DISEASES

| Addition to LCM: | NORMAL GEMM +GM % | BFU-E % | LYMPHOMA GEMM +GM | BFU-E | CML GEMM +GM | BFU-E | HCL LGEMM +LGM | BFU-E |
|---|---|---|---|---|---|---|---|---|
| None | 100(104) | 100(78) | 100(27) | 100(9) | 100(40) | 100(22) | 100(23) | 100(14) |
| IFN-$\alpha_c$ 10 U/ml | 76 | 77 | 40 | 47 | | | 99 | 107 |
| IFN-$\alpha_c$ 100 U/ml | 57 | 27 | 62 | 41 | 39 | 59 | 124 | 124 |
| IFN-$\beta$ 100 U/ml | 87 | 74 | 66 | 42 | 90 | 150 | 165 | 125 |
| IFN-$\beta$ 500 U/ml | | | | | | | 160 | 125 |
| IFN-$\tau$ 100 U/ml | 60 | 38 | | | 99 | 64 | 136 | 106 |
| IFN-$\tau$ 500 U/ml | 53 | 21 | | | | | 89 | 42 |

Total number of colonies in parentheses.
The results show percentage of growth. 5 cases from normal, lymphoma, CML and HCL peripheral blood are shown in the table.

Differential effect of interferons on normal hematopoiesis

When studying the differential effect of interferons on normal hematopoiesis it was found that at 10 U/ml IFN-$\beta$ does not suppress hematopoiesis and in some cases there is an increase in BFU-E from bone marrows (BM). The results with BM cell growth are shown in Table IIa and the results with normal peripheral blood (PB) progenitor cell growth are shown in Table IIb. The increase in erythroic growth was more prominent on monocyte-depleted bone marrow (Table III).

TABLE IIa
DIFFERENTIAL EFFECT OF INTERFERONS ON NORMAL HEMATOPOIESIS

| CELLS | IFN | U/ml | MIX | GM | BFU-E | Meg |
|---|---|---|---|---|---|---|
| Normal BM | — | | 13 | 117 | 78 | 7 |
| | alpha-c | 100 | 8 | 47 | 21 | 7 |
| | beta | 10 | 12 | 100 | 64 | 7 |
| | beta | 100 | 15 | 99 | 58 | 8 |
| | gamma | 100 | 14 | 64 | 30 | 12 |
| Normal BM | — | | 33 | 128 | 121 | 25 |
| | alpha-c | 100 | 22 | 88 | 42 | 12 |
| | beta | 10 | 30 | 131 | 120 | 17 |
| | beta | 100 | 23 | 149 | 104 | 12 |
| | gamma | 100 | 35 | 153 | 90 | 20 |
| Normal BM | — | | 12 | 75 | 45 | 5 |
| | alpha-c | 100 | 6 | 49 | 27 | 3 |
| | beta | 10 | 11 | 72 | 45 | 4 |
| | beta | 100 | 8 | 59 | 43 | 3 |
| | gamma | 100 | 7 | 67 | 34 | 2 |

TABLE IIb

| CELLS | IFN | U/ml | MIX | GM | BFU-E | Meg |
|---|---|---|---|---|---|---|
| Normal PB | — | | 17 | 86 | 53 | 7 |
| | alpha-c | 100 | 9 | 55 | 29 | 6 |
| | beta | 10 | 15 | 82 | 66 | 6 |
| | beta | 100 | 14 | 78 | 49 | 8 |
| | gamma | 100 | 12 | 83 | 40 | 11 |
| Normal PB | — | | 24 | 113 | 67 | 19 |
| | alpha-c | 100 | 11 | 71 | 38 | 13 |
| | beta | 10 | 22 | 115 | 66 | 16 |
| | beta | 100 | 18 | 100 | 55 | 10 |
| | gamma | 100 | | | | |
| Normal PB | — | | 10 | 92 | 47 | 15 |
| | alpha-c | 100 | 6 | 36 | 21 | 8 |
| | beta | 10 | 13 | 120 | 56 | 14 |
| | beta | 100 | 9 | 80 | 40 | 12 |
| | gamma | 100 | 8 | 91 | 28 | 15 |
| Normal PB | — | | 31 | 122 | 73 | 26 |
| | alpha-c | 100 | 25 | 85 | 30 | 17 |
| | beta | 10 | 31 | 126 | 105 | 24 |
| | beta | 100 | 26 | 89 | 70 | 27 |
| | gamma | 100 | 30 | 136 | 70 | 12 |

Cultures 14 days in methyl-cellulose with PHA-LCM

In the experiment shown in Table III, it was also shown that increase in erythropoietin (epo) does not produce increase in BFU-E. The effects of IL-3 were also analyzed on normal bonemarrow and compared to those obtained with IFN-$\beta$ and to the combination of both. When cultures were grown in the presence of PHA-LCM, the addition of rIFN-$\beta$ (10 U/ml) and IL-3 (10 U/ml) induced a 3-fold enhancement on erythroid progenitor growth. However when cultures were grown in the absence of PHA-LCM (that contains many factors) IFN-$\beta$ alone had no effect, while the addition of both IL-3 and IFN-$\beta$ produced a two to three-fold increase on BFU-E growth as compared to IL-3 alone.

TABLE III

| NORMAL BONE MARROW | | | | | | |
|---|---|---|---|---|---|---|
| | – monocytes | | | + monocytes | | |
| | MIX | GM | BFU-E | MIX | GM | BFU-E |
| +LCM | 43 | 5 | 61 | 54 | 5 | 173 |
| 2U epo +LCM | 34 | 11 | 59 | 57 | 6 | 122 |
| Control | 16 | 5 | 20 | 6 | 4 | 2 |
| +LCM + IFN-β | 38 | 16 | 161 | 40 | 9 | 145 |
| 2U epo +LCM + IFN-β | 23 | 15 | 50 | 19 | 7 | 37 |
| +LCM +IL-3 | 75 | 53 | 318 | 27 | 28 | 103 |
| +LCM + IFN-β +IL-3 | 63 | 33 | 284 | 35 | 18 | 95 |
| IFN-β | 10 | 6 | 5 | 8 | 2 | 0 |
| IL-3 | 32 | 3 | 70 | 44 | 12 | 61 |
| IFN-β + IL-3 | 30 | 10 | 184 | 13 | 10 | 31 |

IFN-β (10 Units)
IL-3 (10 Units)

Erythropoietic effect on sideroblastic anemia

Peripheral blood progenitor cells of five patients with sideroblastic anemia were studied. The results are shown in Table IV. rIFN-β at 10 U/ml had a significant growth-promoting effect on BFU-E and CFU-Mix. The increase in BFU-E is of a magnitude of 6-fold and in CFU-mix even higher. A less prominent stimulatory effect was observed for CFU-GM. We then studied the effects of IFNβ at 10 U/ml and IL-3 at 10 U/ml and the combination of both. Table IV shows that an enhancement occurs on BFU-E growth when both factors are present together.

TABLE IV

| Peripheral blood progenitor cell growth in sideroblastic anemia (5 cases) | | | |
|---|---|---|---|
| | MIX | GM | BFU-E |
| PHA-LCM | 5 ± 2 | 32 ± 10 | 3 ± 1 |
| + IFN-β 10 U | 62 ± 6 | 48 ± 6 | 18 ± 3 |
| + IL-3 10 U | 18 ± 2 | 40 ± 8 | 20 ± 5 |
| + IFN-β 10 U + IL-3 10 U | 26 ± 4 | 60 ± 4 | 35 ± 8 |

The results are of duplicate culture plates grown in presence of PHA-LCM. IFN-β and IL-3 are added at day 0.

Erythropoietic effect on refractory anemia

Peripheral blood progenitor cells of five patients with refractory anemia with no evidence of blasts or any sign of preleukemia were studied (Table V). PB progenitor cells were grown as in the sideroblastic group. The results obtained showed again a promoting growth effect on mixed colonies and BFU-E when IFN-β is added at 10 U/ml.

Again an almost additive effect was noted with both IL-3 and IFN-β in cultures. In this group of patients the increase in BFU-E was of lesser degree than in the cases of sideroblastic anemia (two fold versus six). Less increase in the number of CFU-GM was observed. This suggests that the effect is more on the maturation status of the progenitor cells mainly those related to erythropoiesis and not on the "stem cell". The increase on CFU-Mix may be due to the erythroid component present in these colonies.

TABLE V

| Peripheral blood progenitor cell growth in refractory anemia (5 cases) | | | |
|---|---|---|---|
| | MIX | GM | BFU-E |
| PHA-LCM | 3 ± 1 | 16 ± 5 | 6 ± 3 |
| + IFN-β 10 U | 5 ± 2 | 18 ± 5 | 11 ± 3 |
| + IL-3 10 U | 5 ± 1 | 17 ± 4 | 12 ± 4 |
| + IFN-β 10 U + IL-3 10 U | 8 ± 2 | 21 ± 3 | 26 ± 5 |

Results are mean ± SEM duplicate plates.
All cultures are grown with PHA-LCM.

Erythropoietic effect on myelofibrosis

Peripheral blood cells of eight patients with myelofibrosis were studied. Cultures with and without LCM were compared and the effects of IFN-β, IL-3 and their combinations were studied. The results (Table VI) show that IFN-β at 100 U/ml is not suppressive on growth of BFU-E obtained from peripheral blood. A slight (not significant) growth-promoting effect is observed in the presence of LCM while in the absence of LCM there is a clear enhancement effect with the combination of IFN-β and IL-3.

TABLE VI

| THE EFFECT OF IFN-β ON HEMATOPOIESIS IN PATIENTS WITH MYELOFIBROSIS | | | | | | | | |
|---|---|---|---|---|---|---|---|---|
| | COLONIES | | | | | | | |
| | +LCM | | | | –LCM | | | |
| FACTORS | MIX | GM | BFU-E | Mg | MIX | GM | BFU-E | Mg |
| — | 106 | 110 | 131 | 10 | 26 | 19 | 26 | 0 |
| IFN-β 100 U | 160 | 93 | 131 | 5 | 74 | 16 | 30 | 0 |
| IL-3 | 157 | 98 | 209 | 6 | 106 | 22 | 77 | 0 |
| IFN-β + IL-3 | 218 | 90 | 209 | 1 | 170 | 46 | 106 | 1 |
| — | 88 | 72 | 90 | 5 | 41 | 37 | 31 | 2 |
| IFN-β 100 U | 112 | 66 | 91 | 3 | 123 | 35 | 33 | 5 |
| IL-3 | 130 | 71 | 158 | 3 | 150 | 39 | 87 | 5 |
| IFN-β + IL-3 | 285 | 70 | 169 | 2 | 162 | 48 | 112 | 6 |
| — | 54 | 48 | 78 | 12 | 32 | 30 | 41 | 0 |
| IFN-β 100 U | 122 | 48 | 84 | 7 | 107 | 32 | 48 | 7 |
| IL-3 | 107 | 44 | 219 | 11 | 128 | 40 | 103 | 6 |
| IFN-β + IL-3 | 208 | 49 | 235 | 9 | 157 | 65 | 134 | 9 |
| — | 120 | 123 | 147 | 19 | 20 | 11 | 29 | 1 |
| IFN-β 100 U | 133 | 102 | 158 | 17 | 81 | 16 | 30 | 9 |
| IL-3 | 141 | 96 | 196 | 3 | 93 | 28 | 85 | 9 |

TABLE VI-continued

THE EFFECT OF IFN-β ON HEMATOPOIESIS IN PATIENTS WITH MYELOFIBROSIS

| FACTORS | COLONIES | | | | | | | |
|---|---|---|---|---|---|---|---|---|
| | +LCM | | | | −LCM | | | |
| | MIX | GM | BFU-E | Mg | MIX | GM | BFU-E | Mg |
| IFN-β + IL-3 | 197 | 204 | 204 | 11 | 121 | 50 | 97 | 12 |
| — | 75 | 82 | 103 | 8 | 24 | 23 | 19 | 0 |
| IFN-β 100 U | 98 | 73 | 109 | 9 | 79 | 31 | 21 | 0 |
| IL-3 | 109 | 69 | 177 | 7 | 181 | 42 | 57 | 1 |
| IFN-β + IL-3 | 156 | 79 | 184 | 5 | 143 | 52 | 76 | 3 |
| — | 93 | 88 | 113 | 19 | 29 | 19 | 24 | 0 |
| IFN-β 100 U | 116 | 71 | 125 | 7 | 87 | 37 | 26 | 1 |
| IL-3 | 134 | 70 | 191 | 3 | 112 | 45 | 73 | 2 |
| IFN-β + IL-3 | 171 | 99 | 198 | 12 | 126 | 48 | 99 | 2 |
| — | 117 | 94 | 129 | 20 | 49 | 35 | 42 | 2 |
| IFN-β 100 U | 128 | 89 | 138 | 21 | 153 | 51 | 45 | 2 |
| IL-3 | 149 | 95 | 222 | 6 | 161 | 63 | 121 | 4 |
| IFN-β + IL-3 | 207 | 106 | 242 | 15 | 199 | 84 | 158 | 7 |
| — | 69 | 55 | 80 | 13 | 16 | 14 | 17 | 0 |
| IFN-β 100 U | 86 | 61 | 86 | 13 | 66 | 27 | 27 | 3 |
| IL-3 | 101 | 67 | 144 | 16 | 85 | 31 | 48 | 3 |
| IFN-β + IL-3 | 150 | 92 | 201 | 18 | 104 | 45 | 62 | 10 |

Since 1,25-dihydroxy Vit $D_3$ has been implicated in the pathogenesis of the myelofibrosis and some clinical cases have shown some improvement, Vit $D_3$ was used in assessing hematopoietic response measured by colony formation. Table VII shows the results obtained using IFN-β and Vit $D_3$ using identical conditions in the same case.

TABLE VII

EFFECT OF IFN-β AND VITAMIN $D_3$ ON BFU-E FROM PERIPHERAL BLOOD IN MYELOFIBROSIS*

| FACTORS | BFU-E (COLONIES PER $10^5$ CELLS) | |
|---|---|---|
| | WITH LCM | WITHOUT LCM |
| 0 | 0 | 0 |
| IFN-β (100) | 0 | 50 |
| VIT $D_3$ ($10^{-9}$M) | 12 | 21 |

*Blood of a patient with severe myelofibrosis and anemia (hemoglobin of 6 g/dl) and chronic pulmonary disease in need of multiple blood transfusions. Factors were added as described in methods. Results are the mean of duplicate cultures.

The mixed colonies were also increased by IFN-β but this effect was evident only in the absence of PHA-LCM. The reason why the growth-promoting effect of IFN-β here was seen mainly in the absence of LCM is not clear, but it may be assumed that it either points to the presence of production of inhibitors by accessory cells in myelofibrosis patients or to an excess of factors provided both by accessory cells and LCM.

Mixed colonies represent an earlier cell than the granulocytic macrophage progenitor cell and were also scored. It was found that when IFN-β was added to cultures deprived of LCM, it promoted by 6-fold the growth of mixed colonies (Table VIII).

TABLE VIII

EFFECT OF IFN-β ON MIXED COLONY FORMATION IN MYELOFIBROSIS

| FACTORS | CFU-MIX | |
|---|---|---|
| | WITH LCM | WITHOUT LCM |
| 0 | 28 | 30 |
| IFN-β (100) | 27 | 118 |
| VIT $D_3$ ($10^{-9}$M) | 36 | NT |

Cells were plated at $10^5$ cells per ml. Colonies were identified and counted. Mixed colonies were removed with a fine Pasteur pipette and stained. Results are the mean of duplicates.

Treatment of Patients

Patients with sideroblastic anemia, refractory anemia, chronic myeloid leukemia or myelofibrosis diagnosed by clinical parameters, physical findings such as enlarged spleen in myelofibrosis, and typical findings in peripheral blood smears and counts are selected for the treatment, the diagnosis being always confirmed by typical features encountered in these disorders by bone biopsy. Stainings for iron deposits and ringed sideroblasts are routinely performed.

For patients with sideroblastic or refractory anemia or myelofibrosis, absence of overt leukemia, absence of B12 or folate deficiency and no cytotoxic therapy in the past 6 months are requirements for inclusion in the treatment and form part of the diagnostic path. Patients with severe diabetes mellitus or known hypersensitivity of some magnitude are excluded. Hallmarks include ineffective hematopoiesis, peripheral blood cytopenias and hypercellular bone marrow.

The duration of the treatment is of at least 3-4 months of intramuscular IFN-β injection at doses of 2 million units (2 MU) daily for the first month and then twice weekly as a preliminary schedule. The continuation of the treatment will depend on the response of the patients. It will be discontinued for patients developing significant laboratory anomalies during the treatment.

A pretreatment evaluation, including the complete history and physical examination of the patients is performed. The data include their ability to perform in daily life, duration of illness, time of worsening, needs for blood transfusion, lag time between transfusions, responses to chemotherapy and androgens (given for improvement of the anemia), bleeding tendencies and infections.

During the treatment, several laboratory investigations are performed including blood counts and differential counts performed at daily intervals during the first week and thereafter weekly for four months; blood smears of bone marrow aspirates, trephine bone biopsies at the begining of therapy and after four months: biochemical tests evaluating renal and hepatic functions performed weekly and pulmonary function and X rays before and after four months of therapy, unless clinically necessary throughout this period. Size of spleen is confirmed by scanning, and performed bimonthly.

The severity of the disease is ranked by the frequency of requirement of blood transfusions and hemoglobin levels. Cardiac and pulmonary capacity (EKG and pulmonary functions) are monitored before institution of therapy and during the first week (monitor for cardiac arrythmias).

The patients are hospitalized for the first week for follow-up by the physician in charge and their cardiac function monitored as well as any possible adverse reaction. Daily reticulocyte counts are checked during the first four weeks as well as the above mentioned blood tests which are performed daily during the first week and thereafter weekly for the first four weeks and then monthly.

Prior to treatment and after two months, blood and bone marrow are studied as done above in the in vitro studies, i.e. hematopoietic in vitro function is evaluated, including response to IFN-$\beta$, and the results are correlated for validity in prediction by statistical analysis (Mann Whitney U test).

The treatment includes intramuscular injections of IFN-$\beta$, 2 megaunits depending on body area, administered daily for the first month of therapy, and then the dose is reduced to twice weekly.

Side effects, if any, are registered and the treatment is stopped if a major side effect attributable to the treatment is noticed. If there are no major side effects, the decision to continue or stop the treatment is made after 4 months of therapy. Blood transfusions, if necessary, are given based on clinical judgement, namely dyspnea and discomfort due to low hemoglobin levels. Blood pressure and pulse rate are automatically monitored.

The efficacy of the treatment is assessed by the following parameters:

1—increase in hemoglobin levels, red cell count, and reticulocyte counts, as well as the white and platelet counts
2—decrease in needs for blood transfusion
3—shortening the interval period of blood transfusions
4—subjective improvement of clinical symptomatology, less weakness, better performance
5—comparison of hemopoiesis as assessed by bone biopsies performed before and after therapy. Cellularity and types of precursors are monitored as well as erythropoiesis.

Case 1

A 57-year old male patient with chronic myeloid leukemia (CML) for 6 years in chronic phase controlled by conventional chemotherapy including hydrea (hydroxy urea) and myleran (Bussulfan), became refractory to this therapy and did not respond to other chemotherapeutic agents such as thioguanine and cytosar. Because of the development of the known transitional aggressive phase with the appearance of leukemic blasts, and increased discomfort with incapability of walking due to huge spleen and a severe anemia necessitating blood transfusions, the patient was then treated with IFN-beta (InterPharm Laboratories Ltd., Israel) based on laboratory experiments showing an erythropoietic response. His clinical response was excellent with a reduction in the white blood cell count, a disappearance of leukemic blasts from the peripheral blood, increase in hemoglobin to 10-11 g/dl, no more need for blood transfusion and a striking decrease in spleen size. The patient was soon back to his normal activities and continued to receive 5 days weekly 2 MU IFN-beta intra muscularly as the single treatment for several months.

The laboratory tests before the treatment showed the following results: hemoglobin 7g/dl, WBC: 81000, blasts 8-10%, immature myeloid cells; promyelocytes 3%, myelocytes 10%, metamyelocytes 14%, segments 40%, stabs 10%, eosinophils 2%, basophils 8%, monocytes 2%, lymphocytes 4%. The platelet count reached 700.000/mm3. His clinical condition deteriorated, the patient was unable to walk partly because of weakness, partly because of increased difficulty in breathing due to both the anemia and the huge spleen.

The patient began receiving IFN-beta (after approval of the Helsinki Comittee of the hospital and of the Ministry of Health) at a daily dose of 2 million units (2MU) per day. 6 days a week and myleran (Bussulfan) 2 mg/day per os. Two months later, his general feeling improved, he was able to walk and perform his daily activities, the need for blood transfusion disappeared and there were no signs of toxicity at all. The only side effect observed was a very mild flu-like syndrome, common in interferon therapy that was controlled with vitamin C and paracetamol for two weeks. The laboratory exams showed an increase in hemoglobin that occurred progressively until 11.4 g/dl, a decrease in the leucocytes to 10,000 /mm3, normal platelet count, 160,000/mm3. and no blasts in the differential white cell count. The differential count remained typical of chronic phase CML and no basophils were observed. The most striking finding on physical examination was the reduction in spleen size to 3 cm (before: 27 cm) and liver 3 cm (before: 14 cm).

Case 2

A 66-year old woman patient showed an extremely unusual story of 8 years myelofibrosis post-splenectomy with myeloid metaplasia in the liver (huge hepatomegaly) with a megakaryoblastic transformation (which is quite a rare event) refractory to hydroxyurea and necessitating almost weekly blood transfusion, with severe weakness and dyspnea. Treatment with a combination of IFN-beta intramuscular 2 million units per day together with a very low dose of myleran (bussulfan) 2 mg in alternating days improved her general well being, reduced in a moderate way her liver enlargement and prompted a disappearance of the megakaryoblasts. An increase in the reticulocyte count from 3.% to 8% indicated that some erythroid maturation occurred (since the LDH levels decreased and no signs of hemolysis were present). The improvement was evident and the treatment was continued.

Numerous modifications and variations in the practice of the invention are expected to occur to persons skilled in the art. The embodiments herein described are to be interpreted as illustrative and not in a limiting sense.

I claim:

1. Method for the stimulation of erythropoiesis in a patient suffering from a disorder characterized by lack of maturation of progenitor blood cells to red blood cells comprising administering to said patient an erythropoietic effective amount of human Interferon-$\beta$.

2. A method according to claim 1 wherein said patient suffers from a myelodisplastic syndrome.

3. A method according to claim 1 wherein said patient suffers from anemia.

4. A method according to claim 1 wherein said patient suffers from sideroblastic anemia.

5. A method according to claim 1 wherein said patient suffers from refractory anemia.

6. A method according to claim 1 wherein said patient suffers from myelofibrosis.

7. A method according to claim 1 wherein said patient suffers from chronic myelomonocytic leukemia.

8. A method according to claim 1 wherein said patient suffers from chronic myeloid leukemia.

9. A method according to claim 1 wherein said patient suffers from anemia caused by a chronic infectious disorder.

10. A method according to claim 1 wherein said patient suffers from anemia caused by rheumatoid arthritis.

11. A method according to claim 1 wherein the human interferon-$\beta$ is human natural interferon-$\beta$.

12. A method according to claim 1 wherein the human Interferon-$\beta$ is recombinant Interferon-$\beta$.

13. A method according to claim 12 wherein the recombinant interferon-$\beta$ is produced by chinese hamster ovary (CHO) cells.

14. A method according to claim 1 which comprises the administration of 1 to 3 million units daily of interferon-$\beta$.

15. A method according to claim 14 which comprises the administration of 2 million units daily of interferon-$\beta$.

16. A method according to claim 1 which comprises also the administration of an erythropoietic effective amount of interleukin-3.

17. A method according to claim 14 which additionally comprises the administration of an erythropoietic effective amount of interleukin-3.

18. A method according to claim 17, wherein the human interferon-$\beta$ is recombinant human interferon-$\beta$.

* * * * *